United States Patent
Carmon et al.

(10) Patent No.: US 9,164,295 B2
(45) Date of Patent: Oct. 20, 2015

(54) VISION PRESCRIPTION, MEASURING METHOD AND MEASURING APPARATUS, AND A LENS PRODUCTION METHOD

(75) Inventors: Yuval Carmon, Kiryat Tivon (IL); Dan Katzman, Givat Ela (IL)

(73) Assignee: SHAMIR OPTICAL INDUSTRY LTD., Upper Galilee (IL)

( * ) Notice: Subject to any disclaimer, the term of this patent is extended or adjusted under 35 U.S.C. 154(b) by 101 days.

(21) Appl. No.: 13/824,482

(22) PCT Filed: Oct. 3, 2011

(86) PCT No.: PCT/IL2011/000770
§ 371 (c)(1),
(2), (4) Date: Mar. 18, 2013

(87) PCT Pub. No.: WO2012/046230
PCT Pub. Date: Apr. 12, 2012

(65) Prior Publication Data
US 2013/0188143 A1 Jul. 25, 2013

Related U.S. Application Data

(60) Provisional application No. 61/390,333, filed on Oct. 6, 2010.

(51) Int. Cl.
*G02C 7/02* (2006.01)
*G02C 7/06* (2006.01)
*A61B 3/00* (2006.01)
(Continued)

(52) U.S. Cl.
CPC . *G02C 7/027* (2013.01); *A61B 3/00* (2013.01); *A61B 3/0025* (2013.01); *A61B 3/0285* (2013.01); *A61B 3/103* (2013.01); *G02C 7/061* (2013.01)

(58) Field of Classification Search
CPC .......... G02C 7/025; G02C 7/027; G02C 7/061
See application file for complete search history.

(56) References Cited

U.S. PATENT DOCUMENTS

| 5,387,952 A | 2/1995 | Byer |
| 6,655,803 B1 | 12/2003 | Rubinstein et al. |

(Continued)

FOREIGN PATENT DOCUMENTS

| WO | WO2008089998 | 7/2008 |
| WO | WO2010065475 | 6/2010 |

OTHER PUBLICATIONS

Hagele: USA Eyes, "How to Read Eyeglass or Contact Lens Prescription: Detailed explanation of the meaning of an eyeglass or contact lens prescription. The first step to considering Lasik." pp. 1-3. Available as of Oct. 7, 2014. http://www.usaeyes.org/lasik/faq/read-eyeglasses-contacts-prescription.htm.

(Continued)

*Primary Examiner* — Jordan Schwartz
(74) *Attorney, Agent, or Firm* — Dorsey & Whitney LLP

(57) ABSTRACT

A method for determining parameters of the vision of an eye of a patient. The method comprises: constituting a part of a process of making a prescription for a corresponding lens via which the patient is expected to gaze in at least two different directions; and measuring in one of the two directions all of the following parameters of the eye's vision: sphere power, cylinder and cylinder axis, and measuring in the other of the two directions at least two of said parameters.

10 Claims, 6 Drawing Sheets

(51) Int. Cl.
*A61B 3/028* (2006.01)
*A61B 3/103* (2006.01)

(56) References Cited

U.S. PATENT DOCUMENTS

| | | |
|---|---|---|
| 2004/0100618 A1 | 5/2004 | Barker |
| 2006/0244915 A1 | 11/2006 | Clemons et al. |
| 2009/0290121 A1* | 11/2009 | Drobe et al. ............ 351/169 |
| 2011/0085134 A1* | 4/2011 | Allione ............ 351/177 |
| 2012/0188504 A1* | 7/2012 | Petignaud et al. ....... 351/159.74 |

OTHER PUBLICATIONS

Wikipedia: "Corrective Lens" pp. 1-14, Available as of Oct. 7. 2014. http://en.wikipedia.org/wiki/Corrective_lens.

International Search Report and Written Opinion from International Application No. PCT/IL2011/000770 mailed Feb. 9, 2012.

* cited by examiner

|  | Sphere | Cylinder | Axis |
|---|---|---|---|
| OD | -2.75 | -1.25 | x 15 |
| OS | pl | -0.75 | x 85 |

Fig. 1

| Rx | | Spherical | Cylindrical | Axis | Prism | Base |
|---|---|---|---|---|---|---|
| D.V. | O.D. | -2.25 | -.75 | 110 | | |
|  | O.S. | +.50 | -1.00 | 90 | | |
| N.V. | O.D. | +1.50 | | | | |
|  | O.S. | +1.75 | | | | |

| Angle | Rx | | Spherical | Cylindrical | Axis |
|---|---|---|---|---|---|
| | D.V. | O.D. | -2.25 | -.75 | 110 |
| | | O.S. | +.50 | -1.00 | 90 |
| | N.V. | O.D. | +1.50 | -.50 | 120 |
| | | O.S. | +1.75 | -1.25 | 80 |
| +20 | N.V. | O.D. | -2.5 | -.75 | 110 |
| | | O.S. | pl | -1.00 | 90 |
| -60 | N.V. | O.D. | +1.25 | -.50 | 120 |
| | | O.S. | +1.5 | -1.25 | 80 |

Fig. 8

| Vertical Angle | Horizontal Angle | Rx | | Spherical | Cylindrical | Axis |
|---|---|---|---|---|---|---|
| | +1 | O.D. | 0.8 meters | -2.25 | -.75 | 110 |
| | -1 | O.S. | 0.4 meters | +.50 | -1.00 | 90 |
| | +3 | O.D. | 0.6 meters | +1.50 | -.50 | 120 |
| | -3 | O.S. | 0.6 meters | +1.75 | -1.25 | 80 |
| -30 | +32 | O.D. | | -1.00 | -1.00 | 130 |
| | +28 | O.S. | | +.50 | -1.00 | 70 |
| +10 | -28 | O.D. | | +1.50 | -1.75 | 100 |
| +10 | -32 | O.S. | | pl | -.50 | 60 |

VISION PRESCRIPTION, MEASURING METHOD AND MEASURING APPARATUS, AND A LENS PRODUCTION METHOD

FIELD OF THE INVENTION

This invention relates to the field of vision diagnosis and correction.

BACKGROUND OF THE INVENTION

It is generally well known that people suffering from poor visual acuity often find relief by using vision correcting lenses. These may come in the form of corrective contact lenses or corrective lenses fitted into spectacles. In both cases the desired optical characteristics of the lenses (usually sphere power, cylinder and cylinder axis) are determined in the following way: the patient is given a visual acuity test—be it objective (using, for example, an auto-refractometer), or subjective (normally using a trial frame or a phoropter fitted with trial lenses). The outcome of the test is a prescription listing the measured optical properties of the tested eye corresponding to an optimal correction lens for the patient's vision. The prescription can include sets of such optical properties, each normally being referred to as Rx and obtained by at least one measurement of one of the patient's eyes as it gazes at an image (or object), at a standard direction of gaze and distance. In all cases, the optical properties of the tested eye, and indeed the optical properties of the device to be used to correct the malfunctioning eyes are tested when the patient is gazing straight ahead.

Some patients also suffer from Presbyopia (the lack of ability to focus on near objects even if one has corrected vision for objects at infinity), of lacking accommodation. To determine an Rx of a lens for such patient, the patient goes through a further test in which parameters of his eye in the near vision are measured. In this case the patient is usually instructed to read a hand held book using different correctional lenses. The Rx of an optimal correction lens for near vision work is then selected. When obtaining this Rx, the patient is either instructed to look straight ahead when reading or to look in a natural direction of gaze, which is usually to gaze downwards. The Rx found for near work will usually have the same cylinder and axis but have a different value for the sphere power than the Rx for far away objects. The difference between the near and far sphere powers is usually referred to as 'the addition'. This value constitutes an integral part of the prescription for patients that are to be fitted with progressive or bifocal lenses.

SUMMARY OF THE INVENTION

The presently disclosed subject matter relates to a multi-Rx eye prescription, lens design and an apparatus for measuring vision of a patient's eye all connected with the fact that a patient's visual deficiencies depend on the direction of gaze, and therefore, if a lens is designed to correct a patient's vision, for example, in a straight-ahead direction of gaze for far away objects, it will in many cases not be optimal when the patient's direction of gaze changes.

The subject matter of the present application is thus based on the realization that, in the case of spectacle lenses, it is possible to change the optical properties of the correction lens so that the patient may have improved vision in many directions of gaze and not only when gazing straight ahead. This is because when the patient rotates his or her eyes to gaze in a new direction, the pencil of light reaching the center of the pupil is refracted by only a small part of the lens surface. Designing that particular small part of the lens surface to be optimal for the patient's needs in that particular direction of gaze and at a particular distance depending on the patient's needs, provides a vision correction device optimal for more than one direction of gaze.

In accordance with the above, the general methodology from which the presently disclosed subject matter is derived can be therefore summarized as follows:

1. Measure a patient's eye's Rx (sphere power, cylinder, cylinder axis) in many directions of gaze and for objects of varying distances, as may be of any particular need of the patient. For example, such need can be designing spectacles for a driving environment in which many directions of gaze are required for viewing objects at different distances. Another example of such need can be designing spectacles for sporting activities such as basketball, in which the patient uses large eye rotations for viewing far away objects.
2. Design a lens, for example a progressive lens, that optimally corrects the patient's Rx measured in different direction of gaze and for objects of varying distances. For this purpose, one can use the same optimization algorithms that are known for designing progressive lenses that correct the patient's Rx when the patient is staring either straight ahead or gazing down to read. These optimization algorithms optimize the lens surfaces so that the resulting lens has a minimal amount of unwanted aberrations. In much the same way, according to the presently disclosed subject matter, the optimization algorithm can receive as an input the patient's Rx in at least two directions of gaze and consequently calculate the lens surfaces so that the lens will correct the patient's Rx in the at least two directions of gaze while maintaining good optical performance (low aberrations) in other parts of the lens. While in known progressive lenses only the sphere power is changed between the far Rx and the near Rx, in progressive lenses designed in accordance with the presently disclosed subject matter, the full Rx can differ (i.e. sphere power, cylinder and cylinder axis) for each direction of gaze.
3. Manufacture the lens designed as described above. Due to the high inherent customizability of such a lens, one method for producing it can be by using a CNC cutting machine, which is able to process surfaces on a per-patient basis (in the ophthalmic industry, this is typically termed as "freeform" or "direct surfacing" technology).

One aspect of the presently disclosed subject matter thus relates to a method for determining parameters of the vision of an eye of a patient, the method
    constituting a part of a process of making a prescription for a corresponding lens via which the patient is expected to gaze in at least two different directions, and
    comprising measuring in one of the two directions all of the following parameters of the eye's vision: sphere power, cylinder and cylinder axis, and measuring in the other of the two directions at least two of the parameters.

Another aspect of the presently disclosed subject matter relates to a prescription for an eye of a patient expected to gaze in at least two different directions via a progressive addition lens (PAL), comprising:
    at least an indirect indication of the at least two directions of gaze;
    an indication of the eye's sphere power, cylinder and cylinder axis in one of the two directions of gaze; and an indication of at least two of the eye's sphere power, cylinder and cylinder axis, in the other one of the two directions of gaze.

A still another aspect of the presently disclosed subject matter relates to a prescription for an eye of a patient expected to gaze in at least three different directions via a progressive addition lens, comprising:

at least an indirect indication of the at least three directions of gaze;

an indication of the eye's sphere power, cylinder and cylinder axis in one of the three directions of gaze; and an indication of at least one of the eye's sphere power, cylinder and cylinder axis, in each of the other one of the three directions of gaze.

A further aspect of the presently disclosed subject matter relates to a prescription for an eye of a patient expected to gaze in at least two different directions via a single vision lens, comprising:

at least an indirect indication of the at least two directions of gaze;

an indication of the eye's sphere power, cylinder and cylinder axis in one of the two directions of gaze; and an indication of the eye's sphere power in the other one of the two directions of gaze.

Another further aspect of the presently disclosed subject matter relates to a method of producing a lens based on a prescription as defined above, comprising:

designing the lens as having a number of design points corresponding to the number of the directions of gaze indicated in the prescription, the points being defined by the same parameters as those indicated in the prescription for their respective directions of gaze; and manufacturing the lens corresponding to the above design.

A still further aspect of the presently disclosed subject matter relates to an apparatus for measuring vision of an eye of a patient, comprising:

a face positioning device configured for placement of the patient's face so as to bring his/her eye in a fixed position;

a vision measuring device having an optical axis and at least one lens positionable on the axis; and a moving mechanism configured to move at least a part of the vision measuring device relative to the face positioning device such as to orient the optical axis in at least two different directions in each of which the optical axis passes through the fixed position.

In the above method, prescription or apparatus according, the at least two directions can be three or more directions.

In the above apparatus one of more of the following features can be used separately and in any combination:

the moving mechanism can be configured to provide said movement such that each point on the optical axis moves along a trajectory lying on a spherical surface;

the vision measuring device can include at least one lens positioning device configured to position said at least one lens at a desired distance from the fixed position along the optical axis in the at least two different directions thereof;

the vision measuring device can include an automated refractor (i.e. also referred to as auto-refractometer/autorefractor), a phoropter, or any alternative thereof;

the vision measuring device can comprise two or more lenses positionable on the optical axis, each can be any one of a focusing, a defocusing and a collimating lens.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 is an exemplary standard prescription for a patient in a single direction of gaze;

FIG. 2 is an exemplary prescription for a patient in two directions of gaze;

FIG. 7 is an exemplary prescription for a patient, according to one aspect of the presently disclosed subject matter;

FIG. 8 is an exemplary prescription for a patient, according to one aspect of the presently disclosed subject matter;

DETAILED DESCRIPTION OF EMBODIMENTS

Figure 3:
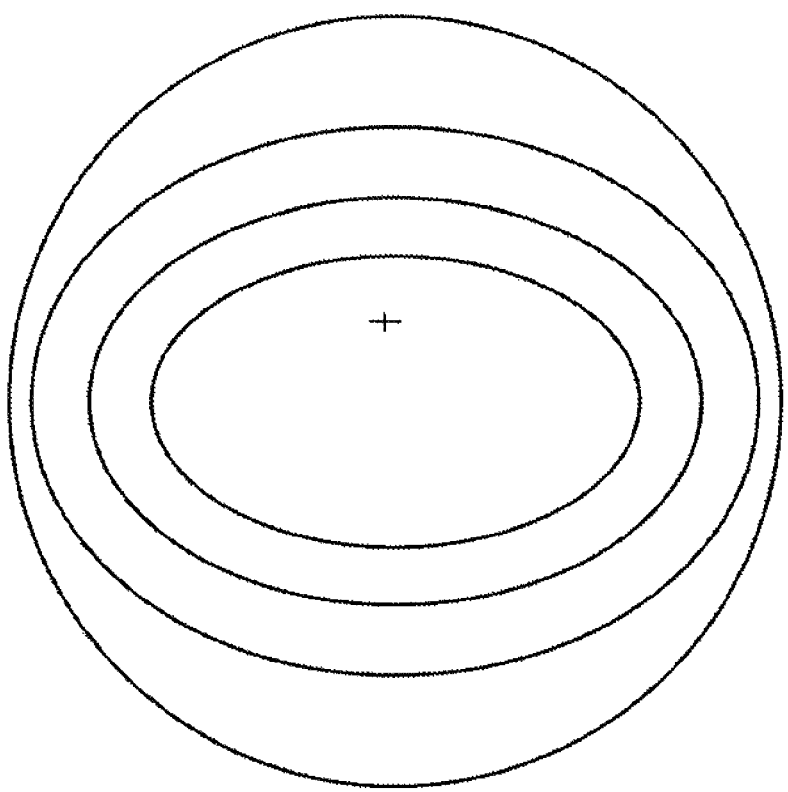
FIGS. 3 to 6 are exemplary lenses with the indication of points corresponding to directions of glaze in which measurements of a patient's vision are performed.

FIG. 1 shows exemplary prior art prescription for single vision lenses for two eyes (OD—right eye, OS—left eye), the prescription referring to the following optical properties of the eye: the spherical power or power (sphere), the astigmatism (cylinder), the cylindrical axis or orientation of the astigmatism (axis), the former two properties being in Diopters, with a typical tolerance of 0.125 Diopter, the latter property being in degrees. The indication 'pl' ('plano') means that there is no refractive error.

FIG. 2 is an exemplary prior art prescription for two bi-focal lenses for two eyes (OD and OS as above), the prescription including optical properties of each eye in far vision (D.V.) and near vision (N.V.), each set of such properties for each eye for each of the far and near vision being designated as Rx (one line in the prescription). The term ADD may also be used in a prescription of this kind to indicate the power to be added for near vision for a bifocal lens in reference to the distance (far) vision (this addition is usually the same for both eyes). The terms Prism and Base are related to image displacement through the lens and are only used for patients with special conditions of vision.

Though not shown in FIGS. 1 and 2, any prior art prescription will also typically indicate the pupillary distance (PD), i.e., the distance between the pupils of the patient's eyes.

The directions of gaze are not specifically indicated in prior art prescriptions as shown in FIGS. 1 and 2, since they are standard as explained below.

For a single vision lens, and for the far vision of a bi-focal or multi-focal lens, measurement is taken when the patient's tested eye gazes straight forward, and the near vision measurement in the latter lens is taken when the patient gazes down to read, the far and near vision directions being represented by corresponding points on the respective lens. The angle of the latter gaze is typically about 30 degrees below the straight forward-vision line. Naturally, in the near vision, directions of gazing of the two eyes of a patient are not parallel and slightly converge as a result of natural ocular behavior. Deficiency in convergence may cause parallax problems. To accommodate the above convergence, a lens is typically produced with a slight horizontal shift of its near-vision point relative to a vertical axis passing through its far-vision point. For near vision measurements the viewed objects are usually at a distance of about 40 cm from the eyes, whereas for far vision measurements the distance is usually about 600 cm. In the above measurements made for a prior art prescription of the kind shown in FIG. 2, the cylinder and the axis are only measured and listed for the far vision Rx and the lenses that are designed based on the prescription in FIG. 2 have the same cylinder and axis for the near vision Rx of each eye.

To prepare a prescription according to one example of the presently disclosed subject matter, a professional (e.g. such as an ophthalmologist, an optometrist, an optician and a technician) performs measurements in several directions of gaze, of which one can be the standard straight-ahead (forward) direction in which the standard set of the eye's parameters (sphere power, cylinder and cylinder axis) as described above is measured, i.e. a standard scenario that is well known in the art. In addition, the professional performs measurements in one or more additional directions of gaze to obtain one or more additional sets of parameters, whose orientation is predetermined, for example, relative to the straight-ahead direction.

The straight-ahead direction in the above case is considered to be the base (or reference) direction, relative to which the orientation of the additional directions of gaze is monitored and registered in the prescription. However, it should be noted that a different direction can be used as the base direction, and this direction does not have to be one of the measured directions of gaze or a direction in which the patient is physically capable of gazing. The base direction can also be an externally predetermined direction which is not directly based on the measured eye of the patient, but rather on an external reference relative to which the patient's eye is positioned in a fixed position.

FIGS. 3 to 6 illustrate exemplary lenses wherein points, which are designed to correspond to respective directions of gaze and corresponding measurements of the eye, are marked by crosses and stars, where the crosses correspond to standard directions of gaze used in conventional vision measurements for making prescriptions, and the stars correspond to additional directions. The cylinder levels between these points and across the lenses are shown as curved lines.

Figure 4:
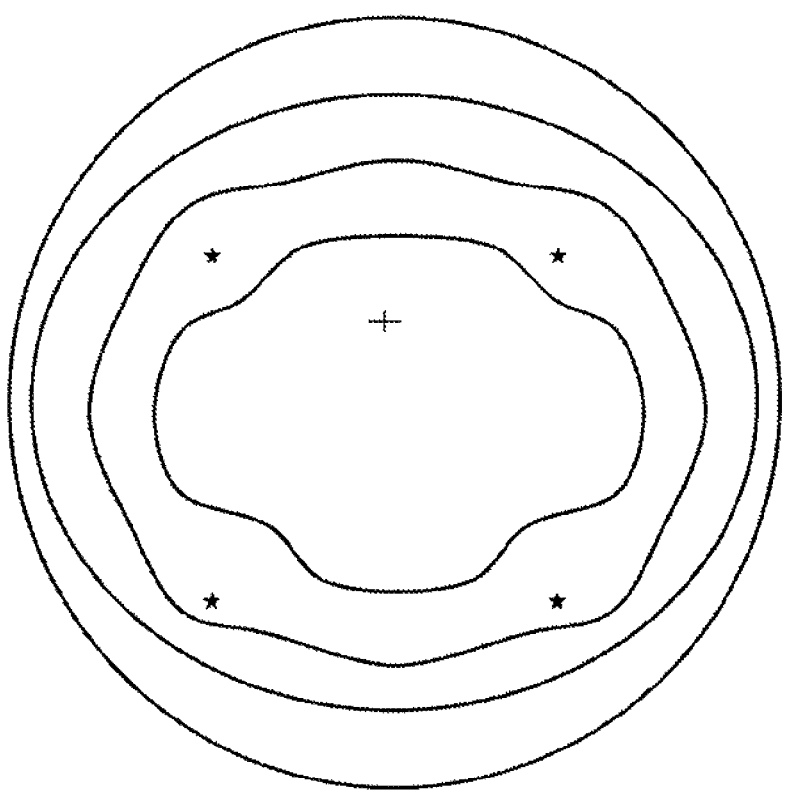
Figure 5:
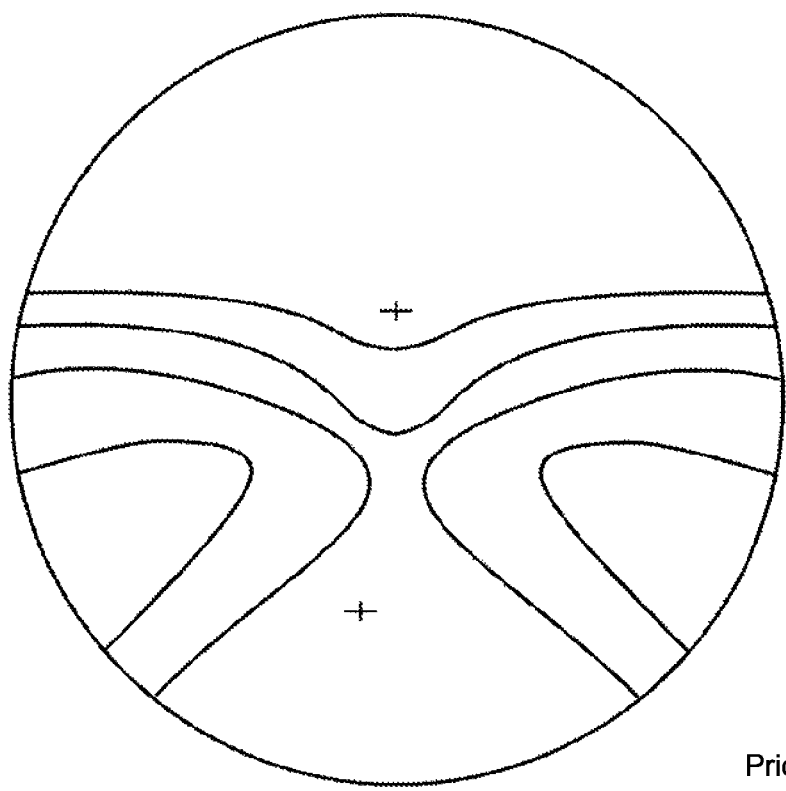
Figure 6:
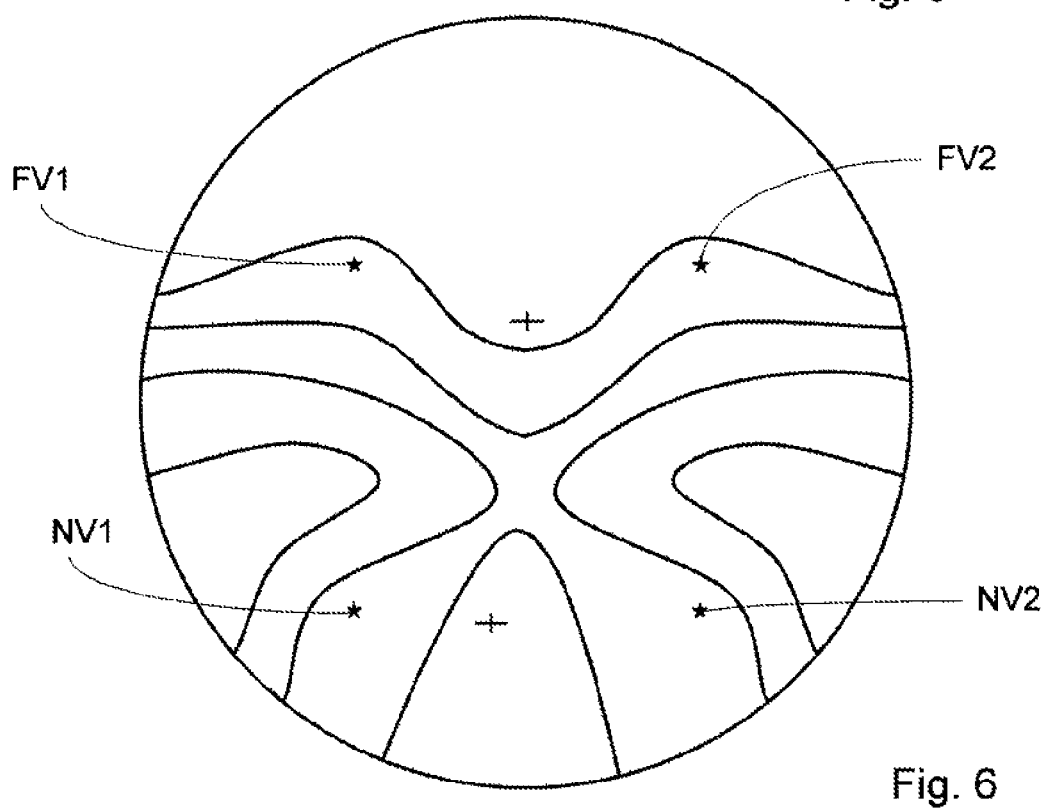

FIGS. 3 and 4 illustrate single vision lenses and FIGS. 5 and 6 illustrate progressive lenses. The lens of FIG. 3 is a standard single vision lens designed for only one direction of gaze, and the lens of FIG. 5 is a standard progressive lens designed for far and near vision. FIGS. 4 and 6 show respective examples of a single vision and a progressive lens designed according to the subject matter of the present application, for gazing in additional four directions, according to prescriptions indicating respective parameters (Rx for each eye) of the patient's vision in each such direction. The additional directions are determined with respect to a base direction which in the present examples is a straight-ahead or forward direction (standard single direction in a single vision lens and the far vision direction in a standard progressive lens).

A process for measuring the patient's vision in the directions different from the base direction, according to the presently disclosed subject matter, for preparing a prescription for lenses such as those illustrated by FIGS. 4 and 6, is similar to that used for preparing a prescription for a progressive addition lens (PAL) or a multi-focal lens, as described above, with the difference being that the presently disclosed process includes at least one of the following steps:
  measurements in directions different from the standard directions (single, forward direction in a single vision lens and far and near vision directions in a PAL), which are specified in the corresponding prescription; and
  in directions other than the base direction (when it is the single, forward direction in a single vision lens and far direction in PAL), optical properties are measured that until now have not been measured in these directions, and they too are listed in the prescription.

For example, for producing a lens such as shown in FIG. 6, with near and far vision according to the presently described process, the cylinder or the cylinder axis or both are measured and included in the prescription not only for the far but also for the near vision, as well as every other direction of vision, thus enabling these parameters to be taken into account for the purposes of producing the prescription based lens.

According to the presently disclosed subject matter, the directions of gaze including the standard directions of gaze can be, for example, divided into two categories: far vision category, where the points corresponding to directions other than the standard far vision direction are located in an upper part of the lens (see, for example, points FV1 and FV2 in FIG. 6); and near vision category, where the points corresponding to directions other than the standard near vision direction are located in a lower part of the lens (see, for example, points NV1 and NV2 in FIG. 6).

For a single vision lens, according to the presently disclosed subject matter, a patient's eye is measured in at least two directions of gaze for either near vision, far vision or in cases when astigmatism correction is required, and a corresponding prescription is issued for a single vision lens. Measurements of the eye performed according to this aspect of the presently disclosed subject matter and the corresponding issued prescription are such that the sphere power in each of the at least two directions of gaze is in the same category of vision. Thus, although the lens is designed substantially similar to a PAL or a multi-focal lens, it is not a conventional prior art PAL lens, as it is not designed for both the far and near vision categories. That is, in the different directions of gaze, the distance of the objects for which vision is measured can only vary to some extent, which is considerably less than for conventional prior art cases of progressive addition and multi-focal lenses wherein far vision is measured in at least one direction of gaze and near vision is measured in at least one other direction of gaze.

In a further example, the sphere powers for the single vision lens prescription are all within a predetermined range of 1 Diopter, and more particularly, the sphere powers can be the same. While the changes in measurements are small for the different directions of gaze, the eye's parameters of sphere power, cylinder and cylinder axis might change to some degree as a function of the direction of gaze, thus the presently disclosed subject matter contributes to a more accurate vision diagnosis and a corrective solution for such changes which is customized for a specific patient's eye.

Furthermore, various applications exist where such single vision lenses offer benefits over the prior art, for example, pilots can require single far vision lenses wherein an upper portion of the lens is configured to have greater far vision power than a lower part or central part of the lens in order to enable the pilot to focus on both the ground in front and below him during landing and on the sky above the horizon where distant objects, such as other aircraft, can be viewed. In another exemplary typical application, one may require a near vision lens for working on a computer which includes viewing a computer screen in front of the person's eyes and viewing they keys on a keyboard which is located closer to the person's eyes and requires him or her to look down at it.

Since, according to the presently disclosed subject matter, generally, a patient's eye is required to gaze in at least two directions, further direct or indirect indications of the direction of gaze can be required. For example, when there are only two directions of gaze which are generally similar to the directions of gaze in a standard eye test, as used in the prior art for preparing the prescription shown in FIG. 2, the directions can still be indicated indirectly by listing the first direction of gaze (straight ahead) and below it the second standard (reading) direction of gaze. However, a new exemplary manner of indicating the respective directions of gaze can be by specifying the vertical angle in which the eye gazes, when the directions of gaze are distributed along the vertical axis with respect to the patient, of course, whose face is presumed to be in a vertical position during the eye test. For example, the patient's eye may be directed in four directions of gaze and measurements thereof are taken in all four directions and (at least) some of the respective predetermined vertical gaze angles are directly indicated in the prescription together with the measured parameters as shown in FIG. 7. In FIG. 7, the first pair of Rx are for far vision of each of a patient's (right and left) eyes and the second pair is for near vision as in the standard case and for standard corresponding directions of gaze (see similar measurements in the prescription in FIG. 2) which are thus indicated indirectly, however, additional measurements are also in two additional directions of gaze of each respective eye. The first additional measurement (two Rx—one for each eye) is taken in a direction of gaze which is 20 degrees above straight forward (presumed to be at a 0 degrees vertical angle), as indicated in the column marked "ANGLE", and the second measurement is taken in when the patient gazes in a direction which is 60 degrees below the straight forward direction.

The gaze convergence of the eyes, due to opposite horizontal angles of the eyes' directions of gaze, depends on the distances of the viewed objects and can be approximately adjusted when the corresponding lenses are designed, as in the prior art.

More precisely, the measurements are taken with respect to the center of the pupil as the optical center of the eye. Thus, the angles of the measuring device or tools are configured accordingly for directions in which the eye gazes while the patient's face remains stationary. The angles of vision (i.e., directions of gaze) in which the patient gazes during the eye test are thus monitored and measured by the professional and subsequently serve as a parameter in the lens design process.

As can further be seen in FIG. 7, the cylinder and the cylinder axis are also measured in more than one direction of gaze. Specifically in FIG. 7, the cylinder and the axis are measured for the second direction of gaze of each eye, and are found to slightly differ for the standard (for a PAL or bi-focal lens) near vision direction of gaze—from the standard far vision direction of gaze (which is the base direction in this example). For the two additional Rx measured for each eye only the spherical power is measured, whereas the cylinder and the axis parameters are not measured, but, are copied from the first (standard) two Rx pairs. Such copying is reasonable in this example because the far vision straight ahead (forward) gaze is relatively close to the gaze which is directed 20 degrees above it, and the standard near vision direction of gaze is relatively close to the final direction of gaze which is directed 60 degrees below the straight ahead gaze.

In FIG. 7 the distances for which the measurements are taken are also indicated, in the standard manner. The straight forward gazing eyes are measured for far vision and for the remaining three directions of gaze, near vision is measured. However, according to the presently disclosed subject matter the distances for which each set of measurements if measured can be different from the standard, and in such cases the distance for which vision is measured for each particular direction of gaze will be indicated, for example, in meters (instead of the abbreviations D.V. and N.V.). As would be apparent to those skilled in the art, these distances can be real, i.e., correspond to the actual distance at which the object, as observed by the patient, is located or can be simulated by optical means, for example, focusing or defocusing lenses positioned along the optical axis of the eye (corresponding to the direction of gaze of the center of the pupil, as mentioned above). For example, a pilot's vision may require correction for viewing objects at great distances, which necessitates indirect measurements of his or her vision.

In a further example of the presently disclosed subject matter, FIG. 8 shows an exemplary prescription wherein the directions of gaze are indicated by two angles. The first direction of gaze is straight ahead—the typical base (reference) direction. To the previously discussed vertical angle, a horizontal angle is added which indicates the angle in which the direction of gaze differs from the base direction. This means that measurements of the patient's eyes are taken also when the patient gazes sideways and are listed in the prescription, allowing the corresponding design and manufacture of better optimized customized lenses for the patient. Further in FIG. 8, it is seen that the prescribed lenses, one for each eye, are generally single vision lenses since all the distances for which vision is measured are in the near vision category. The cylinder and the cylinder axis parameters are also measured, in addition to sphere power, individually for each of the measured directions of gaze.

It should be noted that measuring the directions of gaze in terms of angles can be performed in different coordinate systems. For example, the angles can be taken with respect to axes that are in a plane which is perpendicular to the optical axis of the eye when it gazes straight ahead, thus the movement of the pupil with the spherical surface of the eye is approximated by two-dimensional movement of the center of the pupil in the above plane (the eye is approximated to a point located at its presumed center). Alternatively, a more precise indication can refer to perpendicular axes on a spherical surface which is about similar in size to the spherical surface of the eye. Furthermore, if the indications are by means of angles—these can be measured with respect to other references (base directions), as already noted previously, instead of the standard straight ahead direction of gaze which might not always be an entirely precise reference.

It should also be noted that the presently disclosed subject matter is not restricted to the above exemplary forms of indication of the directions of gaze or the distances of the viewed objects for which measurements are taken. New indirect indications can also be used, for example, sequence listing such is in the prior art prescriptions of PAL or bi-focal lenses.

According to the presently disclosed subject matter, the measured and monitored parameters, which are indicated in the prescription, are subsequently used for the production of customized lenses for the patient. As previously mentioned, lens design algorithms are known in the art and can be used to produce a lens design in accordance with these parameters. One example of such algorithm is disclosed in U.S. Pat. No. 6,655,803, and its description is incorporated herein by reference. Although in the prior art, such algorithms did not receive as input, for example, cylinder and cylinder axis parameters for several directions of gaze—which correspond to several predetermined points of the lens, these algorithms are not restricted to the lesser amount of input from prior art prescriptions, as would be appreciated by those skilled in the art.

Once the design of the lens is complete it serves as input for the manufacturing stage at which the lens can be manufactured using lens manufacturing processes known in the art. For example, by CNC machines as previously mentioned above, or alternatively by creating molds and then casting semi-finished lenses in which only the back surface is processed in order to receive the finished lens, the surface being processed in such a way that the back surface is either a sphere or a torus. In the latter case, the sophisticated surface (designed surface of the lens) is the front surface.

An additional aspect of the presently disclosed subject matter relates to an apparatus for measuring vision of an eye of a patient, which is configured to perform at least some of the above mentioned novel vision measurements, thus obtaining a corresponding eye prescription.

Figure 9:
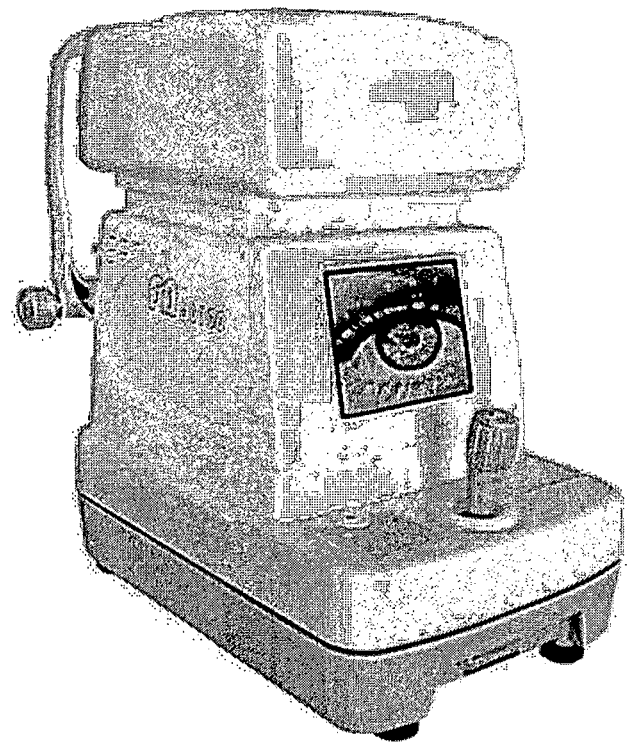
FIG. 9 is an image of an automatic-refractometer.
Figure 10:
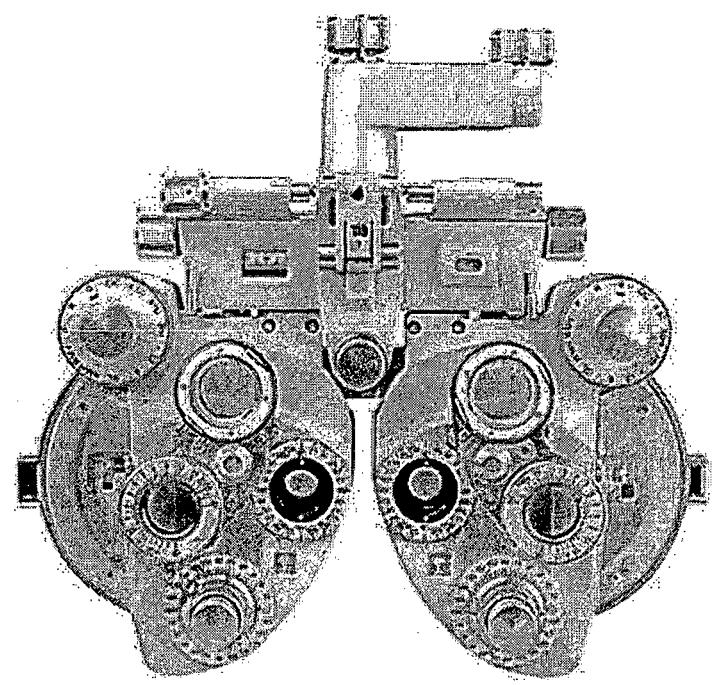
FIG. 10 is an image of a phoropter.

The apparatus includes, generally, a face positioning device. This device is configured for placement of the patient's face so as to bring his/her eye to a fixed position. For example, this device can be similar to the face positioning device which is commonly used as a part of an automated-refractometer, as shown in FIG. 9. Alternatively, it can be in the form of a frame/s so shaped as to make the patient orient his face in an approximately predetermined position when the patient positions his or her eyes adjacent to the apparatus in order to perform the eye test—as is commonly implemented in phoropters, as shown in FIG. 10.

The apparatus further includes a vision measuring device. Both automatic devices (e.g., automated refractor) and devices that are used in conjunction with the patient's responses to the visible images, as well as devices that enable an eye professional to perform a retinoscopy, can form this part of the apparatus. According to the presently disclosed subject matter, these devices can further include lenses that are positionable along its optical axis, such as focusing, collimating or defocusing lenses, used for simulating various distances of the images as viewed by the patient, as will be understood by those skilled in the art.

The vision measuring device of the presently disclosed subject matter can be configured for measuring the vision of a single eye or of both of the patient's eyes, as will be appreciated by those skilled in the art.

In addition, the apparatus includes a moving mechanism configured to move at least a part of the vision measuring device relative to the face positioning device such as to orient the optical axis in at least two different directions, in which the patient is directed to gaze and measurements of the patient's vision are subsequently obtained, in each of which the optical axis passes through the fixed position of the patient's eye. Correspondingly to the nature of the vision measuring device, the movement mechanism can consist of several individual mechanisms and/or adjusted to orient two optical axes of the vision measuring device to both of the patients eyes, when the apparatus is configured for measuring vision of both of the patient's eyes at the same time.

In an embodiment of the apparatus the above movement is limited to a spherical movement so that the optical axis of the vision measuring device is, at all times, directed towards the same point, which presumably corresponds to the position of the patient's eye, and more particularly, to the center of the patient's pupil. The center of the sphere, corresponding to this movement, is selected to be approximately at the center of an average patient's eye when it is in the fixed position.

Figure 11:
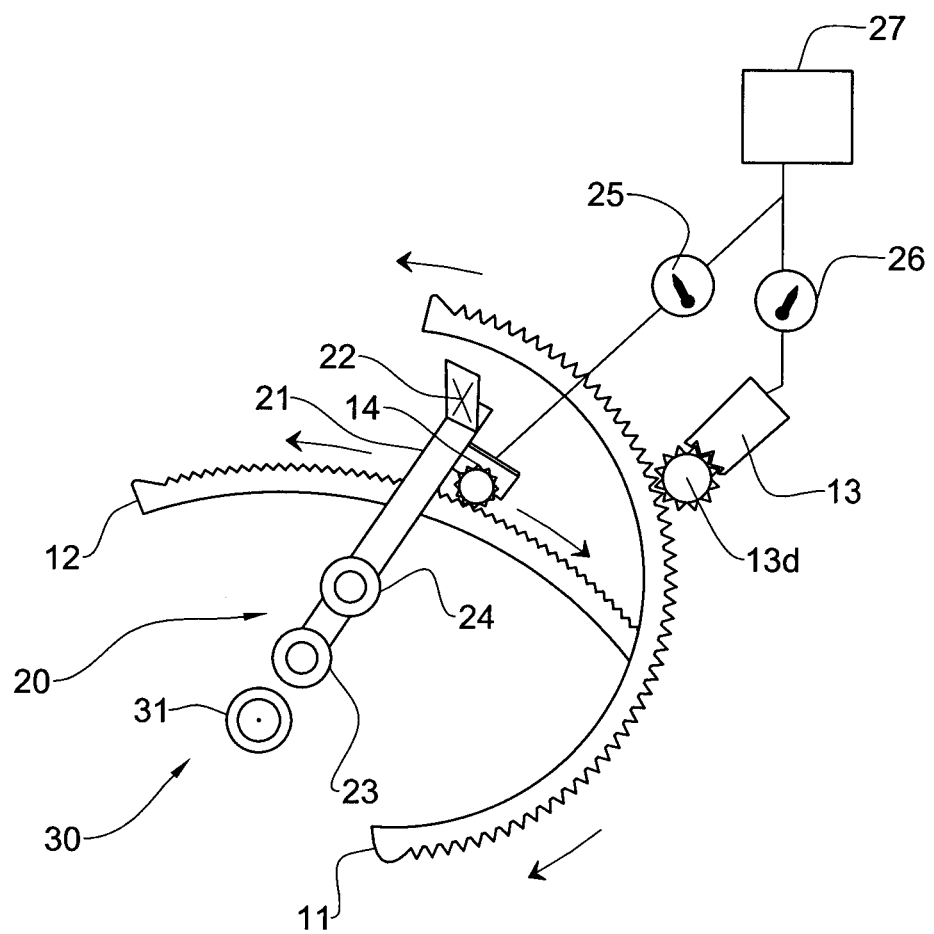
FIG. 11 is one example of an apparatus for measuring vision of an eye of a patient, according to one aspect of the presently disclosed subject matter.

An example of an apparatus according to the above is schematically shown in FIG. 11. Two connected arced members 11 and 12 are formed with cogs and are movable with respect to the stationary rotary actuator 13 and its cog wheel 13a which interact with the arced member 11. A vision measuring device 20 is movable by means of rotary actuator 14 which is attached thereto. The vision measuring device 20 comprises a rod 21, an image (or viewed object) 22 a first lens positioning frame 23 and a second lens positioning frame 24. Positioning device 30, in this example, is schematically shown as a stationary eye frame 31 to which a patient needs to press his or her eye by placing his or her head adjacent to it. The resulting movement of the vision measuring device 20 is such that its optical axis, which passes parallel to the rod 21 and through the lens positioning frames 23 and 24 to the image 22, is always aligned with the center of the eye frame 31 which approximately corresponds to the center of the pupil of an eye pressed to the eye frame 31. The center of the movement is located along the optical axis and slightly in front of the eye frame 31 (i.e., in opposite relation to the position of the vision measuring device 20) where the center of the eye-ball is typically located for an average eye. An additional small adjustment mechanism can of course be used to adjust the optical axis of the vision measuring device 20 for each patient. In the positioning frame 23, a lens can be positioned for assistance in performing the eye test as may be required. In the positioning frame 24, additional lenses can be positioned, as required, for example in order to affect the simulated distance at which the eye views the image 22, as previously mentioned. Angular gauges 25 and 26 show the horizontal and vertical angles, respectively, of the optical axis by being calibrated with the output control readings of the actuators 13 and 14. The angular measurements obtained therefrom can be listed in the prescription. A computer 27 can also be used to record the readings.

The image 22 can be substituted by an automated vision measuring device, such as an auto-refractor, activated at each of the desired orientations of the optical axis to measure the patient's vision in the respective directions of gaze.

In another embodiment of the apparatus, the above movement is configured so the at least a part of the vision measuring device is spatially adjustable such that its optical axis is pointing directly towards the center of the patient's pupil for the different orientations of the device or a part thereof. In an example of such an apparatus, it is further configured to for adjustment of a predetermined distance between a lens positioned on the optical axis of the device and the eye at the fixed position.

In yet another example, the moving mechanism includes an actuator and a frame, the moving mechanism being attached to the frame or to a part of the vision measuring device as to displace it with respect to the frame. The frame can be spherical, so as to enable spherical movement of the vision measuring device or a part thereof. The frame can also, for example, be planar or have an oval shape. Further to this example, the actuator can be used to adjust the distance of the vision measuring device from the frame so as to position it in predetermined orientations with respect to the patient's eye/s. Several actuators can be used to adjust movements in respective axes. The actuators can be, for example, electromechanical, pneumatic or hydraulic actuators, as will be apparent to those skilled in the art.

In further embodiments, the moving mechanism can be manually adjustable by the professional who performs the eye test. For example, one or more lock-and-release holders can be used that are configured to be adjustable by the professional in order to orient the optical axis of the vision measuring device towards the eye, and more particularly, towards the center of the pupil.

The invention claimed is:

1. A method of producing a lens based on a prescription for an eye of a patient expected to gaze in at least two different directions, including: an indication of the at least two different directions of gaze; an indication of eye's sphere power, cylinder and cylinder axis in one of the at least two different directions of gaze one of which differs horizontally from a straight-ahead direction; and an indication of eye's sphere power, cylinder and cylinder axis, in the other one of the at least two different directions of gaze, the method comprising:

designing the lens as having a number of design points corresponding to the at least two different directions of gaze indicated in the prescription, the number of design points being defined by the same parameters as those indicated in the prescription for their respective directions of gaze; and manufacturing the lens corresponding to the above design;

wherein the indications of the eye's sphere power, cylinder and cylinder axis in the at least two directions of gaze are obtained by measurement;

wherein the indication of the at least two directions of gaze includes an indication of a horizontal angle of the at least one of the two directions of gaze, in which the direction of gaze in a horizontal direction differs from the straight-ahead direction.

2. The method according to claim 1, wherein the at least two different directions are three or more different directions.

3. The method according to claim 1, wherein the indication of one of the at least two different directions of gaze is indirect indicating a straight ahead direction of gaze for distance or a downward direction of gaze for reading.

4. The method according to claim 1, wherein the indication of the at least two different directions of gaze is direct with each indicating an angle of gaze.

5. The method according to claim 1, wherein one of the at least two different directions of gaze is a straight direction.

6. A lens based on a prescription for an eye of a patient expected to gaze in at least two different directions, the prescription including: an indication of the at least two different directions of gaze; an indication of eye's sphere power, cylinder and cylinder axis in one of the at least two different directions of gaze one of which differs horizontally from a straight-ahead direction; and an indication of eye's sphere power, cylinder and cylinder axis, in the other one of the at least two different directions of gaze, the lens comprising:

a number of design points corresponding to the directions of gaze indicated in the prescription, the number of design points being defined by the same parameters as those indicated in the prescription for their respective directions of gaze;

wherein the indications of the eye's sphere power, cylinder and cylinder axis in the at least two directions of gaze are obtained by measurement;

wherein the indication of the at least two directions of gaze includes an indication of a horizontal angle of the at least one of the two directions of gaze, in which the direction of gaze in a horizontal direction differs from the straight-ahead direction.

7. The lens according to claim 6, wherein the at least two different directions are three or more different directions.

8. The lens according to claim 6, wherein the indication of one of the at least two different directions of gaze is indirect indicating a straight ahead direction of gaze for distance or a downward direction of gaze for reading.

9. The lens according to claim 6, wherein the indication of the at least two different directions of gaze is direct with each indicating an angle of gaze.

10. The lens according to claim 6, wherein one of the at least two different directions of gaze is a straight direction.

* * * * *